United States Patent [19]

Bartish

[11] 4,102,920

[45] Jul. 25, 1978

[54] PRODUCTION OF CARBOXYLIC ACIDS AND ESTERS

[75] Inventor: Charles M. Bartish, Bethlehem, Pa.

[73] Assignee: Air Products & Chemicals, Inc., Allentown, Pa.

[21] Appl. No.: 759,082

[22] Filed: Jan. 13, 1977

[51] Int. Cl.$^2$ .................... C07C 51/10; C07C 51/12; C07C 67/36; C07C 67/37
[52] U.S. Cl. .................... 260/532; 260/410; 260/410.9 R; 260/413; 260/514 M; 260/515 R; 260/540; 260/541; 560/105; 560/114; 560/204; 560/232
[58] Field of Search ............... 260/532, 488 K, 496, 260/491, 493, 413, 410, 410.9 R, 515 R, 476 R, 514 M, 468 M, 540, 541; 560/114, 232

[56] References Cited

U.S. PATENT DOCUMENTS

| | | | |
|---|---|---|---|
| 3,769,329 | 10/1973 | Paulik et al. | 260/491 |
| 3,946,082 | 3/1976 | McVicker | 260/491 |

*Primary Examiner*—Vivian Garner
*Attorney, Agent, or Firm*—Russell L. Brewer; Barry Moyerman

[57] ABSTRACT

This invention relates to an improved process for the carbonylation of alcohols, esters, ethers and halide derivatives with carbon monoxide in the presence of a catalyst system comprising a Group VIII metal component and a halogen component. The improvement in the process resides in the use of a polydentate chelating phosphorus or arsenic ligand complexed with rhodium as the Group VIII metal component.

10 Claims, No Drawings

PRODUCTION OF CARBOXYLIC ACIDS AND ESTERS

BACKGROUND OF THE INVENTION

1. Field

This invention relates to carbonylation reactions of an alcohol, ether, ester, and halide derivative thereof with carbon monoxide to form carboxylic acids and esters.

2. Description of the Prior Art

Carbonylation processes for the preparation of carboxylic acids and esters from a variety of reactants are well known in the art. One of the better known carbonylation processes involves the synthesis of acetic acid by the reaction of methanol and carbon monoxide in the presence of a catalyst. Various catalyst systems have been reported as being effective for carbonylation processes, but each has had certain disadvantages, for example, instability of the catalyst, lack of product selectivity, low levels of catalyst reactivity, or loss of highly volatile catalyst from the reaction. Particular processes are shown in the following U.S. patents:

U.S. Pat. No. 3,530,168 shows a process for forming carboxylic acid esters by contacting an olefin, carbon monoxide and oxygen with a catalyst comprising a Group VIII noble metal, e.g., palladium complexed with a biphyllic phosphine or arsine ligand, i.e., those having an element with a pair of electrons capable of forming a coordinate bond with a metal atom and simultaneously having the ability to accept electrons from the metal of the catalyst.

U.S. Pat. No. 3,689,533 discloses a process for preparing carboxylic acids and esters by reacting an alcohol and carbon monoxide in the presence of a catalyst comprising the decomposition product of rhodium nitrate and a halogen component.

U.S. Pat. No. 3,769,326 discloses a process for preparing aromatic carboxylic acids and esters by reacting an aromatic alcohol, ester, ether and halide derivative thereof with carbon monoxide in the presence of a catalyst consisting essentially of a rhodium component and a halogen component. Monodentate phosphine and arsine ligands are the only ligands shown.

U.S. Pat. No. 3,887,595 discloses a process for carbonylating olefinic unsaturated hydrocarbons to form acids, esters and acid anhydrides by catalyzing the reaction with a zero valent palladium or platinum complex stabilized with a phosphine ligand.

U.S. Pat. No. 3,917,670 discloses a process for the carbonylation of organomercurials to form carboxylic acids. In that carbonylation process, a catalyst comprising palladium complexed with a phosphine ligand is employed.

U.S. Pat. No. 3,917,677 discloses a process for preparing carboxylic acid esters by reacting an ethylenically unsaturated compound, e.g., propylene, with carbon monoxide and an alcohol in the presence of a catalyst consisting essentially of a rhodium component and a tertiary organophosphorous compound free of halogen.

U.S. Pat. No. 3,923,880 discloses a process for carbonylating alcohol and alcohol derivatives to form carboxylic acids using a catalyst complex containing cations of rhodium or iridium and an anionic moiety other than halide, e.g., tetraaryl borate, phosphate, sulphate, perchlorates, iodates and bromates.

Brodzki et al. in an article appearing in 61 Bull. Chim. Soc. Fr., 61–65 (1976) entitled "Catalytic Properties of Complexes of Precious Metals: Carbonylation of Methanol to Acetic Acid by Rhodium Compounds" discloses the carbonylation of methanol to acetic acid in the presence of a rhodium complex promoted with methyl iodide. The authors conducted the carbonylation with both monodentate and polydentate chelating phosphine ligands, and the conclusion of the authors was that the bidentate ligand is inactive.

SUMMARY OF THE INVENTION

This invention relates to an improved process for forming carboxylic acids and esters by the carbonylation of alcohols, esters, ethers and organo halides. The improvement constituting the basis of this invention resides in the employment of a rhodium complex with a polydentate phosphorus or arsenic chelating ligand as the catalyst at a temperature of from about 160° to about 250° C.

The primary advantage of the catalyst compound of this invention is that the catalyst component is much less volatile than the catalyst species formed when monodentate phosphorus and arsenic ligands are employed as promoters as was done previously in carbonylation reactions. Because the catalyst has lower volatility, it results in substantially reduced loss of catalyst. This factor is extremely important in view of the high cost of the catalyst component and the high concentration thereof required for producing commercial quantities of carboxylic acids and esters.

Another advantage of the invention is that the rate of carbonylation of alcohols and other reactants, although somewhat slower than the rate experienced with a rhodium component stabilized with a monodentate phosphorus ligand, is sufficiently fast for commercial production.

Another advantage of the catalyst is that they are readily soluble and thermally stable making them resistant to deposition of difficult to remove metal in process equipment.

DESCRIPTION OF THE PREFERRED EMBODIMENT

The important feature of this invention is the utilization of a rhodium compound complexed or stabilized with a polydentate chelating phosphorus or arsenic ligand as a catalyst for alcohol carbonylation. The presence of the chelating phosphorus ligand in the rhodium compound reduces the volatility of the compound and thereby reduces the amount of catalyst that must be continually added to the process for synthesis of carboxylic acids and esters.

The chelating, polydentate phosphorus or arsenic ligands of this invention are of a type which, in the presence of carbon monoxide, have a greater binding between the rhodium and phosphorus or arsenic atoms compared to the binding that is experienced between rhodium complexed with monodentate phosphorus or arsenic atoms. Although not intending to be bound by theory, it is believed that it is because of this greater binding between the polydentate chelating phosphorus and arsenic ligands and rhodium that the advantageous properties of the catalyst are achieved. The polydentate phosphorous ligands, in the presence of carbon monoxide, halide and the rhodium compound, result in the formation of a catalyst shown as formula 1, and in the presence of alcohol reactant and acid media for example, a catalyst, as represented by formula 2, is formed. These catalyst species are as follows:

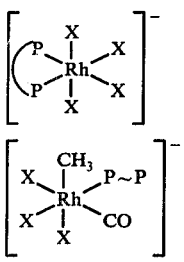

Formula 1

Formula 2 wherein x in Formulas 1, 2, and 3 below is halogen.

On the other hand, as is generally known, the catalyst species which effects carbonylation of alcohols to form esters and acids, where monodentate phosphorus or arsenic ligands are employed, is represented by formula 3. This complex forms readily as the monodentate phosphorus or arsenic ligands are displaced by CO or halide. This particular intermediate catalyst results in the formation of a highly volatile species, as will be explained, which thereby accounts for the losses of rhodium metal from the reactor.

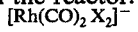  Formula 3

The catalyst component of this invention can be viewed as the reaction product of a rhodium compound and a polydenate phosphine or arsine ligand of the formula:

in which the ratio of ligand to rhodium is at least about 1
wherein:
$R_1$ and $R_3$ are alkenyl groups having from 1 to 6 carbon atoms, alkyl groups having from 1 to 6 carbon atoms, hydrogen atoms, aryl groups, and substituted derivatives thereof;
$R_2$ and $R_4$ are aryl groups and substituted aryl groups;
$P_1$ and $P_2$ are phosphorus and/or arsenic;
A is an arylene group, an alkenyl group having from 2 to 4 carbon atoms and substituted derivatives thereof; and $(CH_2)_n$ where $n$ is from 1-3 where $P_1$ and $P_2$ are phosphorus and 2-4 when $P_1$ or $P_2$ are arsenic.

The rhodium complex with polydentate chelating phosphorus and arsenic ligands can be prepared in a variety of ways. In a typical reaction, a rhodium dicarbonyl chloride dimer and appropriate chelating diphosphine or arsine ligand are dissolved in benzene. The solution of phosphine ligand is added to the rhodium carbonyl solution and carbon monoxide evolves. After evolution of carbon monoxide ceases, an addition of sufficient diethyl ether is made to cause cloudiness. The solution then is cooled and a solid product recovered. Other variations of this general process for preparing complexes of rhodium containing phosphorus and arsenic ligands appear in 8, J. MAGUE, and J. MITCHENER, INORGANIC CHEMISTRY (1), 119-125 (1969).

Examples of rhodium compounds which can be used in forming the rhodium-polydentate phosphine or arsine complex include rhodium trichloride, rhodium tribromide, rhodium trichloridetrihydrate, dirhodium tetracarbonyl dichloride, rhodium tetracarbonyl dibromide, rhodium tris(triphenylphosphino) iodide, rhodium bis(triphenylphosphino) carbonyl chloride, rhodium trinitrate, dimethylchloroiodo tris(triphenylphosphine) rhodium, rhodium oxide, and others commonly used in the art in forming the monodentate complexes.

It is understandable that some of the rhodium phosphine complexes, because of the differences in the ability of the ligands to bind the phosphorus or arsenic atom to the rhodium atom, are more active in catalyzing the carbonylation reaction. Rhodium catalysts having strong binding between ligand and metal, as would be expected where $R_1$, $R_2$, $R_3$ and $R_4$ are methyl groups, are highly inactive; whereas the rhodium catalyst when $R_1$, $R_2$, $R_3$, and $R_4$ are phenyl, which results in weaker binding, has greater activity in catalyzing the reaction. By carefully weakening the binding, as for example by incorporating electron withdrawing groups, e.g., fluorine and nitro groups on a phenyl group, it is possible to weaken the binding even more and enhance activity. What must be avoided is the weakening of the binding to a degree such that carbon monoxide is able to replace both of the phosphorus atoms in the rhodium complex. If that happens, then the intermediate catalyst as shown in formula 3 is formed.

The reaction rate is also affected by the group A in the formula as this also affects binding. For example, when A is $(CH_2)_n$ and $R_1$, $R_2$, $R_3$, and $R_4$ are phenyl, and $P_1$ and $P_2$ are phosphorus, $n$ must be 1, 2, or 3 to produce an effective, non-volatile catalyst. After $n$ exceeds 3, the chelate effect, which stabilizes the non-volatile rhodium complexes, diminishes rapidly. In other words, the binding becomes weaker. As a result, facile substitution of the phosphorus ligands on rhodium by carbon monoxide occurs, leading to a volatile catalyst of the type shown in formula 3. If A is alkenyl, however, four carbon atoms can be in the linkage separating the phosphorus atoms. The binding of this catalyst is sufficiently strong to produce the catalyst of Example 1.

The reactants which may undergo carbonylation in this process to form carboxylic acid and esters are selected from the class consisting of alcohols, alcohol derivatives, ethers, esters, and organo halides having the formula (a) ROH where R is a saturated hydrocarbyl radical having from about 1–20 carbon atoms, (b) $R_1$—O—$R_1$ or $R_1$—CO—$OR_1$ where $R_1$ is a saturated hydrocarbyl radical having from about 1–19 carbon atoms and wherein the total number of carbon atoms in each formula under (b) does not exceed about 20 and (c) R—X where R is a saturated hydrocarbyl radical having from about 1–20 carbon atoms and X is bromine, chlorine or iodine. Examples of reactants from these classes include methanol, ethanol, propanol, isopropanol, butanol, hexanol, cyclohexanol, cyclopentanol, benzylalcohol, higher alcohols such as decanol, dodecanol, nonodecanol; ethers such as methyl ether, ethyl ether, isopropyl ether and butyl ether; acetates such as methyl acetate, ethyl acetate, pentyl acetate, methyl methacrylate, ethyl methacrylate, 2-ethylhexyl methacrylate; and organo halides such as methyl chloride, propyl bromide, heptyl iodide and the like.

As with prior art processes involving the carbonylation of alcohols, ethers, esters, and organohalides, the reaction is carried out by intimately contacting the reactant in either vapor or liquid phase with gaseous carbon monoxide in a liquid reaction medium, generally acidic, containing the rhodium complex of a polydentate chelating phosphorus or arsenic ligand, and a halogen-containing promoting component. In addition, the temperature of the reaction is generally from about 160° to 250° C with preferred temperatures being from about 190° to 210° C. The pressure of carbon monoxide in the reaction generally is in the range of 1 to 15,000 psig, however, pressures of 5 to 1,000 psig are preferred. If the temperature falls below about 160° C, the reaction rate is extremely slow.

The concentration of rhodium-polydentate phosphorus or arsenic ligand used in production of carboxylic acids is generally based on the moles of alcohol reactant employed. In a broad sense, the mole ratio of alcohol reactant to the mole ratio of rhodium-phosphorus or arsenic ligand is from about 20 to about 26,000 with preferred proportions of from about 200 to 1,000. As might be expected from the theory advanced before, as the concentration of the rhodium-polydentate phosphorus or arsenic ligand is increased, the rate of reaction increases. However, concentrations of rhodium metal above about 0.05 preferably about 0.01 moles per mole alcohol reactant do not result in significant operating advantages.

The halogen component used in the catalyst composition is a chlorine, iodine, or bromine providing compound. Its function is to act as a promoter and once an effective proportion of halogen providing component is provided in the reaction medium, the rate of reaction is not substantially influenced by additional quantities. Generally, the concentration of halogen providing component is adjusted to provide about 2 to 50,000 atoms halogen per atom of rhodium and preferably from about 5 to 500 atoms halogen per atom of rhodium. Examples of halogen providing compound include aryl halides, metal halides, ammonium halides, phosphonium halides, arsonium halides, stibonium halides and alkyl or hydrogen halides. Specific examples include methyl iodide, phenyl bromide, ethyl iodide, hydrogen iodide, and so forth.

The following examples are provided to illustrate preferred embodiments in the invention, and are not intended to restrict the scope thereof.

EXAMPLE 1

Di-[1,2-bis(diphenylphosphino)ethane]rhodium(I)-chloride was prepared by adding dropwise a solution of 5.14 mmoles of 1,2-bis(diphenylphosphino)ethane in 25 ml of benzene to 2.57 mmoles of $[Rh(CO)_2Cl]_2$ dissolved in 30 ml of benzene. Vigorous evolution of carbon monoxide occured during the addition of ligand and a yellow precipitate of the crystalline product formed. The crystals were filtered, washed with benzene, and dried in a vacuum. The compound was characterized as di-[1,2-bis(diphenylphosphino)ethane]rhodium(I)chloride by its infrared spectrum and elemental analysis.

EXAMPLE 2

Acetic acid was prepared by adding a mixture of 5g of methanol, 3.2g of 50% aqueous hydriodic acid, 52.5g of acetic acid solvent, and 0.44g of the rhodium catalyst of Example 1 to a pressure vessel. The vessel was sealed, filled with carbon monoxide to a pressure of 750 psig, and heated to 190° C. After a short induction period, methanol carbonylation began, which was allowed to continue until the pressure in the vessel had decreased to 350 psig. The rate of acetic acid formation was $2.9 \times 10^{-4}$ mole/liter/sec. After the reaction was terminated by cooling the vessel contents and releasing pressure, the clear, red-orange solution was removed and analyzed. The yield of acetic acid from methanol was 95% and no significant quantities of by-products were detected.

EXAMPLE 3

Acetic acid was prepared by the method of Example 2 except that the catalyst composition was generated in situ during the conversion of alcohol to acid by charging the autoclave with 0.475 mmole of tris(triphenylphosphino)rhodium(I)chloride and 0.475 mmole of 1,2-bis(diphenylphosphino)ethane. The yield and rate of production of acetic acid were similar to those of Example 2.

EXAMPLE 4

Acetic acid was prepared by the method of Example 3 except the molar ration of 1,2-bis(diphenylphosphino)ethane to rhodium was varied. The results show that there is no significant advantage in rate or product yield in using more than a 1:1 molar ratio of ligand-to-rhodium and further at very high proportions of ligand-to-rhodium, the rate decreases. (Note the high concentration, i.e., 4.75 moles ligand per 0.475 moles Rh.) At high concentrations, e.g., above about 10 moles ligand per mole rhodium, it is believed the ligand competes with the carbon monoxide for the rhodium atom. When less than about 1.0 moles, and generally less than 1 mole ligand per mole rhodium is employed, there is greater loss of metal due to the formation of formula 3 type catalysts. Preferably, the ratio is about 1–3:1 ligand to rhodium.

| mmoles Rh | mmoles Ligand | Rate Mole Rh | Yield, Acetic Acid |
|---|---|---|---|
| 0.475 | 0.475 | 0.78 | 95% |
| 0.475 | 0.710 | 0.65 | 95% |
| 0.475 | 0.950 | 0.66 | 95% |
| 0.475 | 1.90 | 0.70 | 95% |
| 0.475 | 4.75 | 0.30 | 95% |

EXAMPLE 5

Acetic acid was prepared by the method of Example 3 except that a variety of chelating phosphine ligands of the type $(C_6H_5)_2P(CH_2)_nP(C_6H_5)_2$, where $n=1, 3$ and 4 were used. The examples show the effect of $n$ on the rate of acetic acid synthesis.

| Ligand | mmole Rh | mmole Ligand | rate/ mole Rh |
|---|---|---|---|
| dpm | 0.475 | 0.713 | 0.20 |
| dpm | 0.475 | 0.950 | 0.23 |
| dpm | 0.475 | 1.425 | 0.22 |
| dpp | 0.475 | 0.475 | 0.86 |
| dpp | 0.475 | 0.713 | 0.90 |
| dpp | 0.475 | 0.950 | 1.00 |
| dpp | 0.475 | 1.90 | 0.78 |
| dpb | 0.475 | 0.713 | 1.40 |
| dpb | 0.475 | 0.950 | 1.44 |

In the above table and following Examples the following abbreviations have been used to identify the ligand.

| | |
|---|---|
| diphos | 1,2-bis (diphenylphosphino)ethane |
| dpm | bis(diphenylphosphino)methane |
| dpee | cis-1,2-bis(diphenylphosphino)ethylene |
| dpp | 1,3-bis(diphenylphosphino)propane |
| dpb | 1,4-bis(diphenylphosphino)butane |
| triphos | bis(2-phenylphosphinoethyl)phenylphosphine |
| dmpe | 1,2-bis(dimethylphosphino)ethane |
| mppe | 1,2-bis[(methyol)phenylphosphino]ethane |
| dars | 1,2-bis(diphenylarsino)ethane |
| darm | 1,2-bis(diphenylarsino)methane |
| arphos | 1-(diphenylarsino)-2-(diphenylphosphino)- |

| | | |
|---|---|---|
| fos | 1,2-di-[bis(pentafluorophenyl)phosphino]ethane | |

EXAMPLE 6

Acetic acid was prepared by the method of Example 2 except that chelating ligands of the type $R_1R_2PCH_2CH_2PR_1R_2$, $R_1=R_2=CH_3$ and $R_1=CH_3$, $R_2=C_6H_5$, were used. The examples show that the rate of acetic acid synthesis is decreased markedly by the presence of electron donating substituents, i.e., methyl groups on phosphorus.

| Ligand | mmole Rh | mmole Ligand | Rate/mole Rh |
|---|---|---|---|
| mppe | 0.475 | 0.475 | 0.41 |
| mppe | 0.475 | 0.950 | 0.01 |
| dmpe | 0.475 | 0.475 | 0.00 |

EXAMPLE 7

Acetic acid was prepared by the method of Example 3 except that chelating arsine and mixed arsine-phosphine ligands were employed. The ligand bis(diphenylarsino)methane does not give non-volatile carbonylation catalysts as both arsenic atoms are detached and the catalyst in Formula 3 is formed. However, both dars and arphos produce non-volatile catalysts which catalyze acetic acid synthesis at significant rates.

| Ligand | mmole Rh | mmole Ligand | rate/Mole Rh | reaction Temp., °C |
|---|---|---|---|---|
| dars | 0.475 | 0.475 | 0.71 | 192 |
| dars | 0.475 | 0.950 | 0.53 | 192 |
| dars | 0.475 | 1.425 | 0.64 | 192 |
| arphos | 0.475 | 0.475 | 0.80 | 192 |
| arphos | 0.475 | 0.950 | 0.80 | 192 |
| arphos | 0.475 | 1.425 | 0.72 | 192 |
| darm | 0.475 | 0.475 | 2.02 | 195 |
| darm | 0.475 | 0.950 | 1.92 | 195 |
| darm | 0.475 | 1.425 | 1.65 | 195 |

EXAMPLE 8

Acetic Acid was prepared by the method of Example 2 except that the chelating ligand cis-1,2-bis(diphenylphosphino)ethylene was employed. The rate of production of acetic acid was a little slower to that obtained when the chelating ligand was diphos. It is believed this is due to increased binding between rhodium and phosphorus owing to a shorter length between the phosphorus atoms bound to an ethylene group. The yield was 95% or the same as with diphos.

EXAMPLE 9

Acetic Acid was prepared by the method of Example 2 except that the chelating ligand bis(2-phenylphosphinoethyl)phenylphosphine was used. The rate of acetic acid production per mole of rhodium was 0.34.

EXAMPLE 10

Acetic acid was prepared by the method of Example 9 except that propionic acid was used as the solvent. The rate of acetic acid formation per mole of rhodium was 0.50 and the yield of acetic acid was 95%.

EXAMPLE 11

Acetic acid was prepared by the method of Example 9 except the temperature was increased to 210° C. The rate of acetic acid synthesis per mole of rhodium was 0.96.

EXAMPLE 12

The volatility of the rhodium complexes of polydentate chelating phosphine ligands was measured and compared with the volatility of prior art rhodium compounds which form the catalyst species $[Rh(CO)_2X_2]^-$, where X generally is iodine, when complexes of mondentate phosphine ligands are used as starting materials. This latter catalyst species in the presence of carbon monoxide converts to $Rh(CO)_3X$ and $[Rh(CO)_2X]_2$.

Four separate catalyst compositions were evaluated for volatility while at a reduced pressure and moderately high temperature. Catalyst 1 was formed from rhodium trichloride trihydrate and carbon monoxide according to a procedure in Example 4 of U.S. Pat. No. 3,769,329. Catalyst 2, of course, is the catalyst of Example 1. Catalyst 3 is the reaction product of carbon monoxide and Catalyst 1. Catalyst 4 is the reaction product of Catalyst 3, carbon monoxide and methanol formed in a reaction medium containing hydrogen iodide.

The table below gives the volatility data at the respective temperature and pressure and time period. It is clear that the catalyst species formed by complexing a rhodium compound and a monodentate phosphine or arsine ligand is substantially more volatile than the species formed with the chelating phosphine ligands.

TABLE

| | Complex | % Sublimed | Temp, °C | mm Hg | Time |
|---|---|---|---|---|---|
| Catalyst 1 | $[Rh(CO)_2Cl]_2$ | 100% | 92 | 0.10 | 5 min |
| Catalyst 2 | $Rh(diphos)_2Cl$ | 0 | 95 | 0.025 | 1 hr |
| | | 0 | 150 | 0.050 | 1 hr |
| Catalyst 3 | $Rh(diphos)(CO)Cl$ | 0 | 95 | 0.025 | 1 hr |
| | | 0 | 0.025 | 1 | hr |
| Catalyst 4 | $(CH_3CO)Rh(diphos)I_2$ | 0 | 100 | 0.05 | 1 hr |
| | | 0 | 150 | 0.05 | 1 hr |

What is claimed is:

1. In a carbonylation process which comprises contacting a reactant selected from the group having the formula (a) ROH where R is a saturated hydrocarbyl radical having from about 1 to 20 carbon atoms, (b) $R_1$—O—$R_1$ or

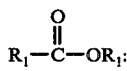

wherein $R_1$ is a saturated hydrocarbyl radical having from about 1 to 19 carbon atoms and wherein the total number of carbon atoms in formulas $R_1$—O—$R_1$ or

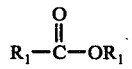

does not exceed about 20 and (c) R—X where R is a saturated hydrocarbyl radical of 1 to 20 carbon atoms and X is a halogen atom selected from the group consisting of bromine, chlorine and iodine, with carbon monoxide, in the presence of a catalyst consisting essentially of (1) a rhodium compound and (2) a halogen component, the improvement which comprises employing as the rhodium compound a rhodium complex formed between a rhodium component and a phosphorus or arsenic ligand of the formula:

in which the molar ratio of chelating ligand to rhodium is at least 1
wherein:
$R_1$ and $R_3$ are alkenyl groups having from 1 to 6 carbon atoms, alkyl groups having from 1 to 6 carbon atoms, hydrogen atoms, phenyl, and substituted phenyl derivatives where the substituent is nitro or fluorine;
$R_2$ and $R_4$ are phenyl and substituted phenyl groups where the substituent is nitro or fluorine;
$P_1$ and $P_2$ are phosphorus or arsenic;
A is an aryl group, an alkenyl group having from 2 to 4 carbon atoms and $(CH_2)_n$ where $n$ is from 1-3 when $P_1$ and $P_2$ are phosphorus and 2-4 when $P_1$ or $P_2$ is arsenic and carrying out said process at a temperature of from about 160° to about 250° C.

2. The process of claim 1 wherein A in said formula is $(CH_2)_n$.

3. The process of claim 2 wherein said reaction is carried out in an aqueous acidic reaction medium.

4. The process of claim 2 wherein $R_1$ is phenyl or a substituted derivative thereof.

5. The process of claim 4 wherein $R_3$ is phenyl or a substituted derivative thereof.

6. The process of claim 5 wherein $n$ is from 1-2 and the ratio of ligand to rhodium is from about 1-3:1.

7. The process of claim 6 wherein said reactant is an alcohol.

8. The process of claim 7 wherein said halogen component is an iodine providing component.

9. The process of claim 8 wherein said reactant alcohol is methanol.

10. The process of claim 9 wherein said process is carried out at a temperature of from about 190° to about 210° C.

* * * * *